United States Patent [19]
Cook et al.

[11] Patent Number: 4,895,144
[45] Date of Patent: Jan. 23, 1990

[54] SUPPLY SYSTEM FOR STERILE FLUIDS AND GASES IN LASER SURGERY

[75] Inventors: Kenneth P. Cook, Blue Bell; Robert M. Bross, Ivyland, both of Pa.

[73] Assignee: Surgical Laser Technologies, Inc., Erlanger, Ky.

[21] Appl. No.: 118,255

[22] Filed: Nov. 9, 1987

[51] Int. Cl.$^4$ .............................................. A61B 17/36
[52] U.S. Cl. .......................................... 606/2; 604/30
[58] Field of Search ............... 128/6, 203.12, 203.16, 128/203.22, 303.1, 207.14, 207.15; 604/27.30, 80, 81, 131, 147, 186, 254, 260; 433/80, 81, 82, 89

[56] References Cited

U.S. PATENT DOCUMENTS

| | | | |
|---|---|---|---|
| 3,794,026 | 2/1974 | Jacobs | 128/207.15 |
| 4,333,454 | 1/1982 | Hargest | 604/30 |
| 4,340,050 | 7/1982 | Noiles | 604/254 |
| 4,493,695 | 1/1985 | Cook | 604/30 |
| 4,503,853 | 3/1985 | Ota et al. | 128/303.1 |
| 4,534,734 | 8/1985 | Lares | 433/82 |
| 4,550,240 | 10/1985 | Toida et al. | 128/303.1 |
| 4,667,655 | 5/1987 | Ogui et al. | 604/27 |
| 4,713,051 | 12/1987 | Steppe et al. | 604/30 |
| 4,715,372 | 12/1987 | Phillppbar et al. | 128/303.1 |

*Primary Examiner*—Max Hindenburg
*Attorney, Agent, or Firm*—Hill, Van Santen, Steadman & Simpson

[57] ABSTRACT

A fluid supply system for gas and sterile liquids consisting of a disposable sterile cartridge that is connected to gas and liquid sources and a common exhaust. The cartridge cooperates with a rotating bearing assembly which pumps the liquid through the system without ever contacting the liquid. The gas sources are provided with means for supplying the gas under pressure to the cartridge. A suitable control selects either the gas or liquid source and a pair of gauges monitor the flow rates of the fluids.

24 Claims, 3 Drawing Sheets

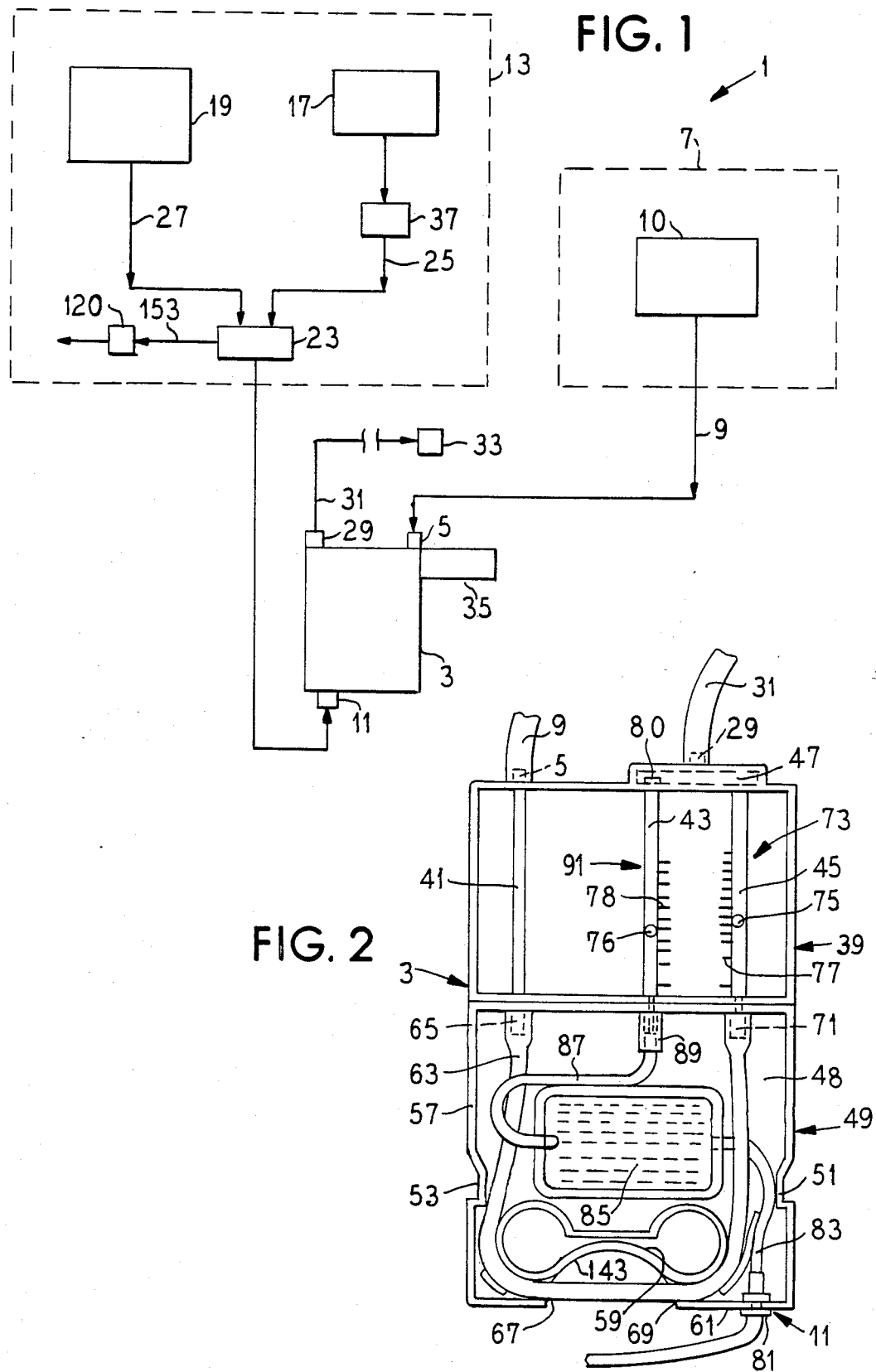

SUPPLY SYSTEM FOR STERILE FLUIDS AND GASES IN LASER SURGERY

BACKGROUND OF THE INVENTION

The invention relates, generally, to laser surgery and, more particularly, to a device for supplying pressurized fluid to a flexible fiber optic guide.

Surgical lasers are typically comprised of a main chassis for generating the laser energy coupled through a flexible fiber optic guide to the surgical instrument. The flexible fiber optic guide consists of an optic fiber through which the laser energy travels and a flexible sleeve arranged coaxially over the optic fiber for the length thereof. The space between the optic fiber and the sleeve acts as an annular conduit for delivering fluid through the guide to the surgical instrument.

The fluid is used to keep debris, generated during the operation procedure, away from the optic fiber and surgical instrument. The fluid also acts as a coolant and is especially beneficial in this regard during so called "contact surgery", where the surgical laser instrument actually contacts the tissue.

The fluid, in these laser systems, flows in an open system from the source through the fiber optic guide to the surgical tip where it is discharged at the operation situs. Because the fluid is discharged at the operation situs, it is critical that the fluid, especially liquid, remains in a sterile condition throughout the supply operation. To insure the sterility of the fluid, the sterile fluid source and the fiber optic guide are made disposable and are replaced after each operation procedure.

The known prior art systems achieve this result by connecting a standard I.V. type bottle directly to the fiber optic guide. The bottle is elevated such that gravitational force propels the liquid through the system. While this rudimentary system maintains the sterility of the liquid, the use of gravity to propel the liquid makes it very difficult to select or regulate the flow rate of the liquid. Of course, variances in the flow rate of the fluid can have serious repercussions in the type of sensitive surgical operations in which these laser surgical instruments are used. Moreover, in order to sterilize the flow rate indicators of the prior art they must be dismantled. Thus, because these prior art devices must be sterilized before each use, their upkeep and maintenance is very expensive.

An example of a known type of cassette for a surgical system is disclosed in U.S. Pat. No. 4,493,695 issued to Cook. Cook's apparatus is designed to simplify the "hook up" of the various wires and plugs normally associated with a microsurgical suction system by isolating the various connections in a single disposable cassette. However, this apparatus does not provide a controllable pumping means for varying the flow rate of the fluid. Cook merely uses a "gate" for restricting the liquid path. Moreover, Cook does not disclose a gas delivery system that is controllable in conjunction with a liquid delivery system.

SUMMARY OF THE INVENTION

The present invention overcomes the above noted shortcomings of the prior art by providing a fluid supply apparatus that propels the fluid through the laser system at controllable rates while maintaining the sterility of the fluid.

The invention consists of a disposable sterile cartridge that couples the fluid supply to the fiber optic guide. The cartridge and its associated pumping apparatus are designed such that the liquid fluid can be pumped through the system without exiting the sterile environment comprised of the source, the cartridge and the fiber optic guide. Each of these components are disposable such that they can be replaced after each operative procedure.

The system also includes a gas fluid supply that is connected to the fiber optic guide through the disposable cartridge. The system is controllable such that either the liquid fluid supply or the gas fluid supply may be connected to the fiber optic guide. The flow rates of the fluids are able to be precisely regulated using this novel supply system.

OBJECTS OF THE INVENTION

It is a general object of the invention to provide an improved supply system for sterile fluids.

It is another object of the invention to provide a supply system for sterile fluids in which a pumping apparatus is used t propel the fluid.

It is a further object of the invention to provide a supply system for sterile fluids where it is possible to select from a plurality of fluid sources.

It is still a further object of the invention to provide a supply system for sterile fluids where the flow rates of the fluids can be precisely regulated.

It is yet another object of the invention to provide a supply system for sterile fluids where the components contacting the sterile fluid are disposable.

Other objects of the invention, in addition to those set forth above will become apparent, to one of ordinary skill in the art, from the following disclosure.

BRIEF DESCRIPTION OF THE DRAWINGS

FIG. 1 shows a schematic diagram of the various components of the invention;

FIG. 2 shows a front view of the cartridge of FIG. 2 with its front half removed to provide a supply system for sterile fluids in which a pumping apparatus is used to propel the fluid;

DETAILED DESCRIPTION OF THE INVENTION

Figure 3:
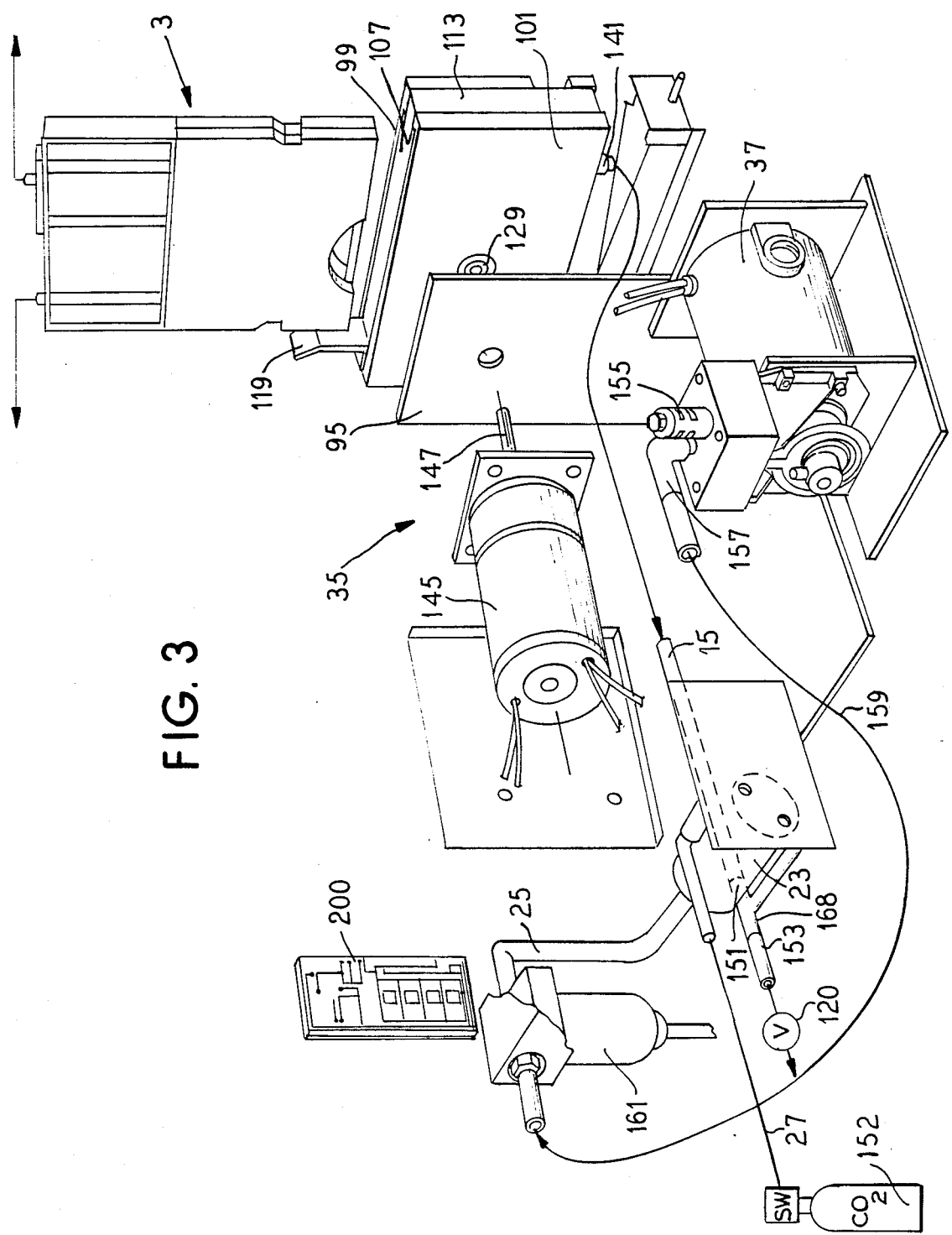
FIG. 3 shows an exploded view of the components of the invention.

The fluid supply system of the invention is shown schematically at 1 in FIG. 1 and includes a disposable sterile cartridge 3 having a first input port 5 connected to a sterile liquid supply 7 by conduit 9. A second input port 11 formed on the cartridge 3 is connected to a gas supply 13 by a conduit 15. The gas supply 13 includes two alternate gas sources 17 and 19 that are connected to a solenoid actuated valve 23 by conduits 25 and 27, respectively. The valve 23 can be activated to connect either on of the two gas fluid sources to the conduit 15.

The cartridge also includes a single output port 29 that is connected to the fiber optic guide 31. A surgical instrument 33 is located at the distal end of the guide 31. A first pumping mechanism 35 is associated with the cartridge 3 for pumping liquid from the liquid supply 7 to the fiber optic guide 31 and a second pumping mechanism 37 is associated with the first gas source 17 to pump gas from the gas supply 13 to the fiber optic guide, as will hereinafter be described.

The cartridge 3, shown in FIGS. 2 and 3, consists of an upper section 39 formed of transparent plastic material including conduit sections 41, 43 and 45. Conduit section 41 terminates at its one end in input port 5 that is connected through conduit 9 to a liquid source 10. The liquid source 10 could be, for example, a conventional I.V. bottle. Conduit sections 43 and 45 terminate at their one ends in a chamber 47 that, in turn, exhausts through output port 29 to the fiber optic guide 31.

Integrally joined with upper section 39 is lower section 49 formed of an opaque molded plastic. lower section 49 is molded in two halves that, when joined together, form a hollow chamber 48. Lower section 49 includes notched recesses 51 and 53 formed in opposite sidewalls 55 and 57, respectively, and an arcuate recess 59 having a semicircular bearing surface 143 formed in the bottom wall 61.

FIG. 2 shows the cartridge 3 with one half of the lower section 49 removed to expose its internal structure. A first end of a flexible conduit 63 is connected to port 65 formed at the end of conduit section 41 opposite input port 5. The flexible conduit section 63 extends from port 65 and is sealably connected to port 71 formed at a first end of conduit section 45. A portion of conduit section 63 extends externally of the cartridge 3 in the area of arcuate recess 59, the function of which will be hereinafter described.

Conduit section 45 forms a portion of gauge 73 that includes a float 75 slidable within conduit section 45 to cooperate with graduated markings 77 formed in upper section 39 to thereby indicate the flow rate of the liquid entering the fiber optic guide 31.

The cartridge 3 further includes the gas input port 11 that consists of a pliable rubber nipple 81 which is able to be connected to the gas fluid source 13, as will hereinafter be described. The nipple 81 is air tightly connected to a first flexible conduit section 83 that, in turn, is connected to a filter 85. Filter 85 is connected to a second flexible conduit section 87 that is sealably connected to port 89 formed at a first end of conduit section 43. Conduit section 43 forms a portion of gauge 91 that is identical in construction to gauge 73 including float 76 and graduated markings 78, and gives the low rate of the gas entering the optic fiber guide 31. A suitable one way valve arrangement 80 is used to prevent the back-flow of fluid from the chamber 47 into the conduit 43.

Figure 4:
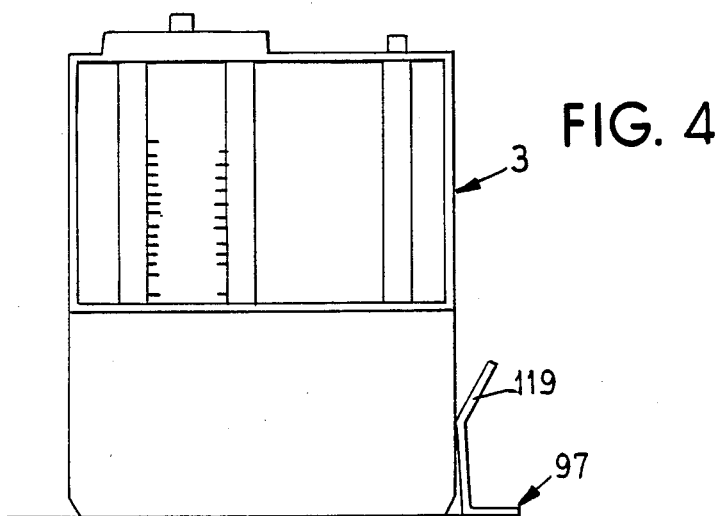
FIG. 4 shows a front view of the cartridge receptacle with the cartridge inserted.
Figure 5:
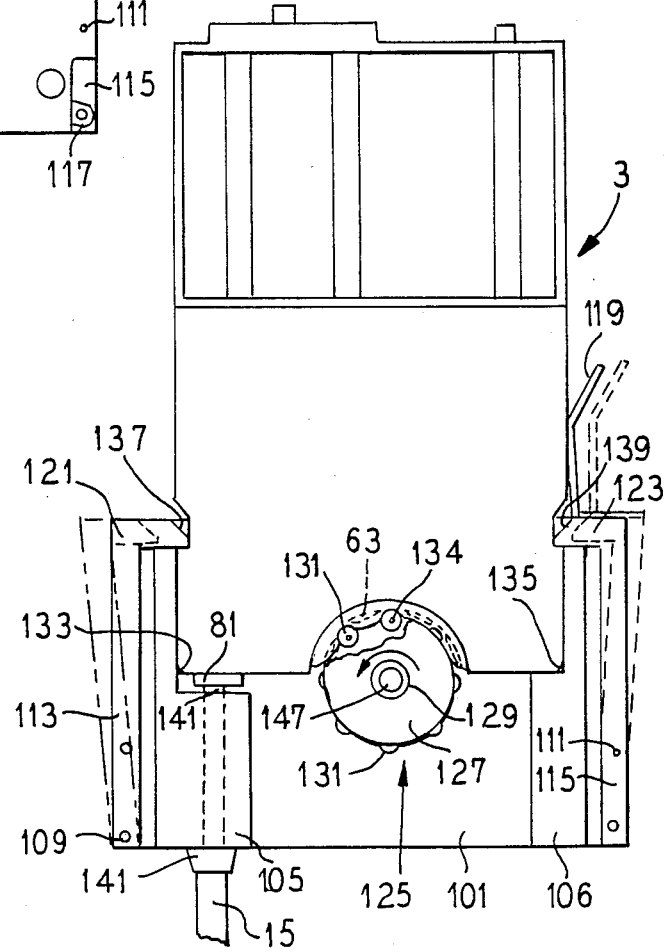
FIG. 5 shows a view comparable to that of FIG. 4, where the outer wall of the receptacle has been removed.

The pumping mechanism 35 associated with cartridge 3 for propelling the liquid is shown generally at 93 in FIGS. 3 through 5. The pumping mechanism 35 includes a cartridge receptacle 97 that slideably receives the cartridge 3. The receptacle 97 includes a front wall 99, a back wall 101, and a pair of L-shaped side walls 105 and 106 arranged to form a cavity 107 into which the cartridge 3 can be inserted.

A pair of arm members 113 and 115 are pivotably mounted on shafts 109 and 111, respectively, and are operatively joined together by a link 117 such that application of a force to the arm members pivots them in unison away from cavity 107 to the dashed line position of FIG. 5. A tension spring (not shown) returns the arm members 113 and 115 to the solid line position of FIG. 5 when the force is removed. The arm members 113 and 115 include inwardly extending fingers 121 and 123, respectively, that extend into the area of cavity 107 to cooperate with the notched recesses 51 and 53, formed in the cartridge 3, to thereby lock the cartridge into receptacle 97.

The receptacle 97 further includes a rotating bearing cam 125 that comprises a wheel 127 fixedly secured to shaft 129. The shaft 129 is journaled in bearing assemblies 130 and 132 located, opposite one another, in the front and back walls 99 and 101 such that the rotation of shaft 129 results in the rotation of wheel 127. A plurality of cylindrical bearings 131 are rotatably supported at regular intervals about the periphery of wheel 127 with their axes of rotation 134 arranged parallel to the axis of rotation of shaft 129.

The cartridge 3 is dimensioned such that the lower section 39 can be inserted in cavity 107. As the cartridge 3 is inserted into cavity 107 the corners 133 and 135 of the lower section 39 contact camming surfaces 137 and 139 formed on the inwardly extending fingers 121 and 123, respectively, to thereby rotate the arm members 113 and 115 to the open position shown in dashed line FIG. 5. When the cartridge 3 has been fully inserted into the cavity 107 a tension spring (not shown) pivots the arm members 113 and 115 to their upright positions to thereby lock the cartridge 3 into receptacle 97 by the engagement of fingers 121 and 123 with recesses 51 and 53, respectively. To remove the cartridge 3 from the receptacle 97, a force is applied to the lever 119 to thereby pivot fingers 121 and 123 out of engagement with recesses 51 and 53. The cartridge 3 can then be easily withdrawn from cavity 107.

As shown in FIG. 5, when the cartridge 3 is in the locked position within cavity 97, the nipple 81 sealably engages port 141 located in the L shaped side wall 105 of receptacle 97. Port 141 is connected to the gas supply conduit 15 to thereby connect the cartridge 3 to the gas supply 13. Moreover, the arcuate recess 59 is dimensioned so as to be received over the rotating bearing cam assembly 125 such that the exposed length of flexible conduit 63 is trapped between the cylindrical bearings 131 and the semicircular bearing surface 143.

A peristaltic motor 145, shown in FIG. 3, is fixedly secured to frame member 95 such that its output shaft 147 is received within the shaft 129. The output shaft 147 and shaft 129 are keyed together such that rotation of the output shaft 147 results in rotation of the bearing cam 125 in the direction of arrow A. The cylindrical bearings 131 deform the exposed length of conduit 63 against the arcuate bearing surface 143 as the bearing cam 125 rotates to thereby pump the liquid fluid from supply 7 to the fiber optic guide 31. It should be noted that when the bearing cam 125 is not rotating, it pinches the flexible conduit against the arcuate bearing surface such that back flow of fluid through the liquid supply is prohibited.

As is evident from the preceding description the novel design of this delivery system allows the liquid fluid to be pumped without it ever exiting the enclosed, disposable, sterile system comprising the fluid supply 7, cartridge 3 and fiber optic guide 31. Once one operative procedure is completed the supply 7, cartridge 3, and fiber optic guide 31 are disposed of and replaced by sterile ones thereof for the next operative procedure. Since the other non-disposable pumping mechanisms of the invention never contact the liquid they can be reused without the need for a separate sterilization procedure or the danger of infection of the sterile fluid.

The gas supply system will now be described in more detail with particular reference to FIGS. 1-4. As shown in FIG. 1, the gas supply 13 includes two separate sources 17 and 19. In the preferred form of the invention, the first source 17 is air from the atmosphere and the second source is gas from a pressurized container, such as a carbon dioxide tank. It should be noted that both sources 17 and 19 could be gases from sources other than those described.

The first source 17 uses a diaphragm pump 37 to intake air form the atmosphere through filtered vent 155 and to exhaust it under pressure at port 157 into conduit 159. Conduit 159 is connected to a vapor collector 161 that, in turn, exhausts to conduit 25.

Since the second gas source 19 originates, preferably, at a pressurized container 152, shown in FIG. 3, it is not necessary to use a separate pump to propel the gas. Therefore, the pressurized container exhausts directly into conduit 27.

Both conduit 25, from the first source 17, and conduit 27, from the second source 19, are connected to conduit 15 through the solenoid activated valve 23. Valve 23 is energized to selectively couple either the first source 17 or the second source 19 with exhaust port 151. Exhaust port 151 is, in turn, connected to port 141, located in the side wall 105 of the cartridge receptacle 97, through conduit 15. In a preferred form of the invention a microswitch, located at the connection of conduit 27 with the gas source 19, will automatically activate valve 23 to connect the gas source 19 with port 141. Thus alternate ones of the gas sources 17 and 19 can be coupled to the gas supply line of the cartridge 3. The solenoid activated valve 23 further includes a port 168 that is connected to a needle valve 120 through conduit 153 that acts as a bleed for controlling the supply of fluid from pump 37.

Because the gas supply 13 and the liquid supply 7 discharge through the cartridge 3 and the cartridge 3 is provided with flow rate monitoring gauges 73 and 91, it is a very simple matter to regulate the fluid flow. Suitable controls 200 are provided to regulate the bleed of needle valve 170, the output of the pressurized container 152 and the speed of peristaltic motor 145. Thus, an exact output of gas, liquid or a combination thereof may be easily obtained.

While the novel supply system of the invention has been described with particular reference to a laser surgical device, it should be noted that this supply system has utility in any applications where the integrity or sterility of the fluid is critical. Numerous changes in the details and construction of the combination and arrangement of parts will be apparent without departing form the spirit and scope of the invention.

What is claimed is:

1. A supply system for transporting sterile liquids and gases for use in laser surgery or other medical applications comprising:
   (a) a disposable sterile cartridge having a gas input, a liquid input, and a common output;
   (b) a gas supply connected to said gas input for delivering gas thereto;
   (c) a liquid supply connected to said liquid input for delivering liquid thereto;
   (d) means for pressurizing the gas of said gas supply;
   (e) means external to and separate from said cartridge and cooperating therewith to pump the liquid of said liquid supply through the cartridge from the liquid input to the common output while maintaining the sterility of the liquid therein.

2. A supply system according to claim 1, wherein said gas supply includes a plurality of gas sources.

3. A supply system according to claim 2, wherein suitable control means can select gas from one of said plurality of gas sources to be delivered to said gas imput.

4. A supply system according to claim 1, wherein said means for pressurizing said gas and said means for pumping said liquid are controllable such that the flow rate of the gas and liquid to said common output can be regulated.

5. A supply system according to claim 1, further including a pair of gauges formed in said cartridge for indicating the flow rates of the gas and liquid.

6. A supply system for transporting sterile liquids and gases for use in laser surgery or other medical applications, comprising:
   (a) a disposable sterile cartridge having a gas input port, a liquid input port, and a common output port, first conduit means connecting said liquid input port to said common output port and a second conduit means connecting said gas input port to said common output, said first conduit means including a length of exposed flexible conduit extending externally of said cartridge;
   (b) third conduit means connecting a liquid supply to said liquid input port for delivering liquid thereto;
   (c) fourth conduit means for delivering gas from a gas supply to said gas input port
   (d) means for pressurizing the gas of said gas supply;
   (e) means external to and separate from said cartridge and cooperating therewith for pumping the liquid through the system, said pumping means including a movable bearing assembly that contacts said length of flexible conduit to deform said conduit and thereby pump the liquid, and a means for moving said bearing assembly.

7. A supply system according to claim 6, wherein said pumping means further includes a receptacle configured to receive said cartridge, said receptacle including a port engageable with said gas input port of said cartridge to thereby connect said fourth conduit means to said gas input port.

8. A supply system according to claim 7, wherein said receptacle further includes a means to releaseably lock said cartridge in said receptacle.

9. A supply system according to claim 6, wherein said cartridge further includes a bearing surface on its outer periphery adjacent said length of flexible conduit such that said movable bearing deforms said length of conduit against said bearing surface.

10. A supply system according to claim 9, wherein said bearing surface is an arcuate recess and said movable bearing assembly includes a rotating wheel mounted in said receptacle such that when said cartridge is inserted in said receptacle said arcuate recess nests over the rotating wheel to trap said length of flexible conduit therebetween.

11. A supply system according to claim 10, wherein said rotating wheel further includes cylindrical bearings arranged along the outer periphery thereof to contact said length of flexible conduit.

12. A supply system according to claim 6, wherein said driving means is a peristaltic motor.

13. A supply system according to claim 6, wherein said cartridge further includes gauges formed one each in said first and second conduit means to indicate the flow rate of the liquid and gas adjacent said common output port.

14. A supply system according to claim 6, wherein said output port is connected to a fibre optic guide.

15. A supply system according to claim 6, wherein said common output port has a chamber into which the first and second conduit means exhaust such that a mixture of gas and liquid can be exhausted through said common output port.

16. A supply system according to claim 6, wherein said gas supply includes a plurality of gas sources connected to said conduit means through a valve such that gas from one of said plurality of gas sources may be delivered to said gas input port.

17. A supply system according to claim 16, wherein one of said plurality of gas sources is the atmosphere and said means for pressurizing said gas is a diaphragm pump.

18. A supply system according to claim 16, wherein one of said plurality of gas sources is a gas from a pressurized container.

19. A supply system according to claim 16, wherein said valve is solenoid activated.

20. A supply system according to claim 17, wherein said control means regulates the output of said pumping means and said pressurizing means.

21. A supply system according to claim 6, further including control means for regulating the flow rate of gas and liquid through said system.

22. A supply system according to claim 6, wherein said second conduit means include a filter for purifying said gas.

23. A supply system for transporting sterile liquids and gases for use in laser surgery or other medical applications comprising a housing having a receptacle thereon for receiving a disposable sterile cartridge therein; a cartridge for insertion into the receptacle, said cartridge having an output port and at least one input port, conduit means connecting each input port to the common output port; means for providing a source of pressurized gas; means in the housing, and external to and separate from the cartridge, and cooperating with said cartridge when received in the receptacle for pumping the liquid from an input port to the output port whenever a supply of liquid is connected to the input port whereby sterile fluid traversing the cartridge shall remain sterile.

24. The supply system for transporting sterile liquids and gases of claim 23 wherein at least one input port is a liquid input port and wherein the conduit connecting said input and common output ports includes a length of flexible tubing extending externally of the cartridge and wherein the means for pumping the liquid includes a movable assembly that contacts the length of flexible tubing to deform said tubing and thereby to pump the sterile or other liquid through the cartridge.

* * * * *